United States Patent [19]

Lewis et al.

[11] Patent Number: 4,861,938
[45] Date of Patent: Aug. 29, 1989

[54] CHEMICAL CONVERSION PROCESS

[75] Inventors: Jeffrey M. O. Lewis; William H. Henstock, both of Charleston, W. Va.

[73] Assignee: UOP, Des Plaines, Ill.

[21] Appl. No.: 70,578

[22] Filed: Jul. 7, 1987

[51] Int. Cl.$^4$ .............................................. C07C 1/00
[52] U.S. Cl. ..................... 585/640; 585/638; 585/641; 585/533; 502/25; 502/26; 502/38; 502/55; 502/56; 208/101; 208/104
[58] Field of Search ............. 585/640, 533, 641, 638; 502/25, 26, 38, 55, 56; 208/109

[56] References Cited

U.S. PATENT DOCUMENTS

| | | | |
|---|---|---|---|
| 2,755,231 | 7/1956 | Blanding et al. | 502/55 |
| 3,088,983 | 5/1963 | Rosenthal | 500/55 |
| 3,450,644 | 6/1964 | Lanewala | 502/38 |
| 4,079,005 | 3/1978 | Tan et al. | 210/52 |
| 4,079,095 | 3/1978 | Givens et al. | 585/640 |
| 4,190,554 | 2/1980 | Yamauchi et al. | 502/25 |
| 4,238,631 | 12/1980 | Daviduk et al. | 585/469 |
| 4,300,011 | 11/1981 | Rollmann | 585/467 |
| 4,359,595 | 11/1982 | Rollmann | 585/640 |
| 4,393,265 | 7/1983 | Bonifaz | 502/38 |
| 4,423,274 | 12/1983 | Daviduk et al. | 585/640 |
| 4,440,871 | 4/1984 | Lok et al. | 502/214 |
| 4,499,327 | 2/1985 | Kaiser | 585/640 |
| 4,550,090 | 10/1985 | Degnan et al. | 502/25 |
| 4,574,044 | 3/1986 | Krug | 500/55 |
| 4,677,242 | 6/1987 | Kaiser | 585/640 |

*Primary Examiner*—H. M. S. Sneed
*Assistant Examiner*—Helane Myers
*Attorney, Agent, or Firm*—Thomas K. McBride; John G. Tolomei; Warren K. Volles

[57] ABSTRACT

A process for converting a feedstock containing 1 to about 6 carbon atoms per molecule which includes (a) contacting the feedstock with a solid composition comprising a crystalline microporous three dimensional solid catalyst having pores and being capable of promoting the conversion, and matrix material at conditions effective to convert the feedstock, to produce at least one desired product, and to at least partially deactivate the solid composition; (b) contacting the deactivated solid composition with regeneration medium at conditions to at least partially regenerate the solid composition; and (c) repeating step (a), the improvement which comprises (d) contacting the regenerated solid composition prior to step (c) to condition the regenerated solid composition to have increased effectiveness in step (c).

42 Claims, No Drawings

CHEMICAL CONVERSION PROCESS

FIELD OF THE INVENTION

This invention relates to a chemical conversion process employing a catalyst. More particularly, the invention relates to such a chemical conversion process employing certain defined catalysts which provides outstanding results.

BACKGROUND OF THE INVENTION

Chemical conversion employing solid catalysts are often conducted using a fixed, ebullating, moving or fluidized bed of catalyst-containing particles. Also, catalyst/liquid slurry reaction systems may be utilized. See commonly assigned U.S. patent applications Ser. Nos. 070,579, 070,574 and 070,575, each filed July 7, 1987. Each of these applications is incorporated in its entirety by reference herein.

Crystalline microporous three dimensional solid catalysts or CMSCs, i.e., catalysts which promote chemical reactions of molecules having selected sizes, shapes or transition states, include naturally occurring molecular sieves and synthetic molecular sieves, together referred to as molecular sieves, and layered clays.

CMSC-containing particles often include one or more matrix materials, such as binders and fillers, to provide a desired property or properties to the particles. These matrix materials often promote undesirable chemical reactions or otherwise detrimentally affect the catalytic performance of the CMSC. It would be advantageous to reduce the deleterious effect of such matrix materials on the catalytic performance or effectiveness of solid compositions containing CMSC and one or more of such matrix materials.

Methanol is readily producible from coal and other raw materials by the use of well-known commerciall processes. For example, synthesis gas can be obtained by the combustion of any carbonaceous material including coal or any organic material such as hydrocarbons, carbohydrates and the like. The synthesis gas can be manufactured into methanol by a well known heterogeneous catalytic reaction.

"Hydrocarbons from Methanol" by Clarence D. Chang, published by Marcel Dekker, Inc. N.Y. (1983) presents a survey and summary of the technology described by its title. Chang discussed methanol to olefin conversion in the presence of molecular sieves at pages 21-26. The examples given by Chang as suitable molecular sieves for converting methanol to olefins are Chabazite, erionite, and synthetic zeolite ZK-5.

U.S. Pat. Nos. 4,238,631; and 4,423,274 disclose processes for converting methanol to olefin-enriched or gasoline boiling range hydrocarbons in the presence of fluid catalyst particles having a zeolite with a pore opening of at least 5 angstroms. These zeolites are distinguished by virtue of having an effective pore size intermediate between the small pore Linde A and the large pore Linde X, i.e., the pore windows of the structure are the size which would be provided by 10 member rings of silicon atoms interconnected by oxygen atoms. These zeolites include ZSM-5, ZSM-11, ZSM-12, ZSM-23, ZSM-35, ZSM-38, and ZSM-48. These patents disclose that such intermediate pore size zeolites can be utilized by maintaining a high coke level on the catalyst, in the range of 5 to 20 weight %, to preferentially produce olefins, U.S. Pat. No. 4,079,095 discloses a process for making light olefins from methanol using ZSM-34, which is a zeolite having a pore size somewhat smaller than the zeolites described in the other patents noted in this paragraph. However, no olefin selectivity advantage for maintaining a high coke level was disclosed when using the smaller pore size ZSM-34 zeolite.

U.S. Pat. Nos. 4,300,011 and 4,359,595 disclose processes for alkylating aromatics and converting methanol to gasoline and/or olefins (among other reactions) catalyzed by the above-noted intermediate sized zeolites with bulky heterocyclic organic nitrogen compounds, e.g., quinoline. These patents disclose that the production of unwanted products is suppressed. These patents disclose that the nitrogen compounds may be effective as heat transfer mediums or solvents for the reaction. Neither patent discloses smaller pore zeolites, catalyst regeneration nor slurry reactions.

Among the CMSCs that can be used to promote converting methanol to olefins are non-zeolitic molecular sieves such as aluminophosphates or ALPOs, in particular silicoaluminophosphates or SAPOs disclosed in U.S. Pat. No. 4,440,871. U.S. Pat. No. 4,499,327, issued Feb. 12, 1985 discloses processes for catalytically converting methanol to light olefins using SAPOs at effective process conditions. This U.S. Patent and EPC Publication are each incorporated in its entirety by reference herein.

SUMMARY OF THE INVENTION

A process for catalytically converting a feedstock has been discovered. In one broad aspect, the present process involves converting a feedstock containing 1 to about 6 carbon atoms per molecule with a solid composition, e.g., solid particles, comprising crystalline microporous three dimensional solid catalyst or CMSC having the ability to promote the conversion and matrix material component at conditions effective to convert the feedstock and to produce at least one desired product. The present improvement comprises conditioning at least a portion of this solid composition prior to and/or during the feedstock/solid composition contacting to provide a solid composition having increased effectiveness in the feedstock/solid composition contacting.

DISCUSSION OF THE INVENTION

The present catalytic conversion process provides substantial advantages. For example, the often relatively nonselective catalytic activity of the matrix material, e.g., binder and filler, component of the solid composition can be substantially reduced or even substantially eliminated by employing the present conditioning step. This benefit is achieved without substantially adversely impacting on the structure or desired functioning of the matrix material. This conditioning step, which is preferably separate and apart from the conventional catalyst regeneration step, can result in more effective feedstock utilization and increased desired product yeilds. In many instances, the conditioning step involves the use of relatively inexpensive materials and/or relatively small amounts of such materials. In short, the present invention can provide a cost effective processing route to improved yields of desired products.

In one embodiment, the feedstock/solid composition contacting further involves at least partially deactivating the solid composition, e.g., by the disposition of carbonaceous deposit material on the solid composition. This deactivation causes the solid composition to be less active in promoting feedstock conversion, e.g., to the desired product. The deactivated solid composition is contacted with regeneration medium, e.g., an oxygen-containing gaseous medium, at conditions effective to at least partially regenerate the solid composition, i.e., to the least partially restore the activity to the solid composition to promote feedstock conversion, e.g., to the desired product. The feedstock/solid composition contacting is then repeated. In this embodiment, the present improvement comprises contacting the regenerated catalyst prior to repeating the feedstock/solid composition contacting to condition the regenerated solid composition to have increased effectiveness in the repeated feedstock/solid composition contacting relative to the regenerated solid composition without the present conditioning.

In another embodiment, the present improvement comprises contacting at least one component, e.g., at least one matrix material component, of the solid composition prior to the feedstock/solid composition contacting to provide the solid composition with increased effectiveness in the feedstock/solid composition contacting.

In a further embodiment, the solid composition during the feedstock/solid composition contacting is present as solid particles in the fluidized state or in a fixed bed, preferably in the fluidized state. In this embodiment, the present improvement comprises conducting the feedstock/solid particles contacting in the presence of at least one added conditioning agent in an amount effective to improve the performance of the solid particles in the feedstock/solid particles contacting, provided that the conditioning agent is substantially incapable of entering the pores of the CMSC. Thus, the conditioning agent can beneficially affect the matrix material component of the solid particles, while having substantially no adverse effect on the CMSC component of the solid particles.

Each of the above three embodiments may be practiced independently, i.e., without reference to the other two embodiments. However, any two or all three of these embodiments may be practiced at one time, e.g., in the same commercial operation. In other words, these embodiments are not necessarily exclusive of each other and may be advantageously practiced in various combinations.

As noted above, CMSCs are those which promote chemical reactions of molecules having selected sizes, shapes or transition states. That is, CMSCs are materials which promote chemical reactions of feedstock molecules which conform to a given molecular size, molecular shape of molecular transition state constraint. Different CMSC have different size/shape/transition state constraints depending on the physical structure and chemical composition, for example, the average effective diameter of the pores, of the CMSC. Thus, the particular CMSC chosen for use depends, for example, on the particular feedstock employed, and on the particular chemical conversion (reaction) and product desired. Preferably, the CMSC has a substantially uniform pore structure, e.g., substantially uniformly sized and shaped pores. CMSCs include, for example, layered clays; zeolitic molecular sieves and non-zeolitic molecular sieves of NZMSs.

The presently useful NZMSs include molecular sieves embraced by an empirical chemical composition, on an anhydrous basis, expressed by the formula:

$$mR:(Q_wAl_xP_yS_{iz})O_2 \qquad (I)$$

where "Q" represents at least one element present as a framework oxide unit "$QO_2{}^n$" with charge "n" where "n" may be $-3, -2, -1, 0$ or $+1$; "R" represents at least one graphic templating agent present on the intracrystalline pore system; "m" represents the molar amount of "R" present per mole of $(Q_wAl_xP_ySi_z)O_2$ and has a value from zero to about 0.3; and "w", "x", "y" and "z" represent the mole fractions of $QO_2{}^n$, $AlO_2{}^-$; $PO_2{}^+$, $SiO_2$, respectively, present as framework oxide units. "Q" is characterized as an element having a mean "T-O" distance in tetrahedral oxide structures between about 1.51 Å and about 2.06 Å. "Q" has a cation electronegativity between about 125 kcal/g-atom to about 310 kcal/gm-atom and "Q" is capable of forming stable Q—O—P, Q—O—Al or Q—O—Q bonds in crystalline three dimensional oxide structures having a "Q—O" bond dissociation energy greater than about 59 kcal/g-atom at 298° K.[1]; and "w", "x", "y" and "z" represent the mole fractions of "Q", aluminum, phosphorus and silicon, respectively, present as framework oxides said mole fractions being within the limiting compositional values or points as follows:

w is equal to 0 to 99 mole percent;
y is equal to 1 to 99 mole percent;
x is equal to 1 to 99 mole percent; and
z is equal to 0 to 99 mole percent.

[1] See the discussion at pages 8a, 8b and 8c of EPC Publication 0 159 624, published Oct. 30, 1985, about the characterization of "EL" and "M". Such are equivalen to Q as used herein.

The "Q" of the "QAPSO" molecular sieves of formula (I) may be defined as representing at least one element capable of forming a framework tetrahedral oxide and may be one of the elements arsenic, beryllium, boron, chromium, cobalt, gallium, germanium, iron, lithium, magnesium, manganese, titanium, vanadium and zinc. Combinations of the elements are contemplated as representing Q, and to the extent such combinations are present in the structure of a QAPSO they may be present in molar fractions of the Q component in the range of 1 to 99 percent thereof. It should be noted that formula (I) contemplates the non-existence of Q and Si. In such case, the operative structure is that of aluminophosphate or AlPO4. Where z has a positive value, then the operative structure is that of silicoaluminophosphate or SAPO. Thus, the term CAPSO does not perforce represent that the elements Q and S (actually Si) are present. When Q is a multiplicity of elements, then to the extent the elements present are as herein contemplated, the operative structure is that of the ELAPSO's or ELAPO's or MeAPO's or MeAPSO's, as herein discussed. However, in the contemplation that molecular sieves of the QAPSO variety will be invented in which Q will be another element or elements, then it is the intention to embrace the same as a suitable molecular sieve for the practice of this invention.

Illustrations of QAPSO compositions and structures are the various compositions and structures described in the patents and patent applications set forth in Table A, which follows, and by Flanigen et.al., in the paper entitled, "Aluminophosphate Molecular Sieves and the Periodic Table," published in the "New Developments and Zeolite Science Technology" Proceedings of the 7th International Zeolite Conference, edited by Y. Murakami, A. Sijima and J. W. Ward, pages 103–112 (1986):

TABLE A
Subject Matter of Patent or Patent Application
Patent or Pat. Applic. No.

U.S. Pat. No. 4,567,029

MAPO's are crystalline metal aluminophosphates having a three-dimensional microporous framework structure of $MO_2^{-2}$, $AlO_2^-$ and $PO_2^+$ tetrahedral units and having an empirical chemical composition on an anhydrous basis expressed by the formula $mR:(M_xAl_yP_z)O_2$; where R represents at least one organic templating agent present in the intracrystalline pore system; m has a typical value of from 0 to 0.3 and represents the moles of R present per mole at $(M_xAl_yP_z)O_2$; M represents magnesium, manganese, zinc or cobalt, x, y and z represent the mole fractions of M, aluminum and phosphorus, respectively, present as tetrahedral oxides. The fractions are such that they are within a tetragonal compositional area defined by points ABC and D of FIG. 1 of the drawings of the patent.

This patent, at column 6, describes the use of aluminophosphates as a source of phosphorus (lines 26-28) and as a source of aluminum (lines 38-40), and the use of seed crystals to aid in the crystallization of the desired molecule sieve (lines 59-63). Example 85 depicts the use of MAPO-36 as a seed for making MnAPO-36. The chemical composition of the MnAPO-36 fails to reveal the presence of any magnesium.

U.S. Pat. No. 4,440,871

SAPO molecular sieves are a general class of microporous crystalline silicoaluminophosphates. The pores have a nominal diameter of greater than about 3 Å. The "essentially empirical composition" is $mR:(Si_xAl_yP_z)O_2$, where R represents at least one organic templating agent present in the intracrystalline pore system; m has a typical value of from 0 to 0.3 and represents the moles of R present per mole of $(Si_xAl_yP_z)O_2$; x, y and z represent the mole fractions of silicon, aluminum and phosphorus, respectively, present as tetrahedral oxides. The fractions are such that they are within a pentagonal compositional area defined by points A, B, C, D and E of the ternary diagram of FIG. 1 and preferably within the pentagonal compositional area defined by points a, b, c, d and e of FIG. 2, of the drawings of the patent. The SAPO molecular sieves have a characteristic x-ray powder diffraction pattern which contains at least the d-spacings set forth in any one of Tables I, III, V, VII, IX, XI, XIII, XV, XVII, XIX, XXI, XXIII or XXV of the patent. Further, the as-synthesized crystalline silicoaluminophosphates of the patent may be calcined at a temperature sufficiently high to remove at least some of any organic templating agent present in the intracrystalline pore system as a result of such synthesis. The silicoaluminophosphates are generally referred to therein as "SAPO", as a class, or as "SAPO-n" wherein "n" is an integer denoting a particular SAPO as its preparation is reported in the patent.

The U.S. patent speaks at column 8, lines 12-16 of employing seed crystals to generate SAPO species. That technique is described in examples 22, 51 and 53.

U.S. Ser. No. 600,312 filed Apr. 13, 1984, now U.S. Pat. No. 4,793,984 commonly assigned, EPC Public. 0 159 624, published Oct. 30, 1985

ELAPSO molecular sieves have the units $ELO_2^n$, $AlO_2^-$, $PO_2^+$, $SiO_2$ in the framework structure and have an empirical chemical composition on an anhydrous basis expressed by the formula:

$$mR:(EL_wAl_xP_ySi_z)O_2$$

where "EL" represents at least one element present as a framework oxide unit "$ELO_2^n$" with charge "n" where "n" may be $-3$, $-2$, $-1$, 0 or $+1$; "R" represents at least one organic templating agent present on the intracrystalline pore system; "m" represents the molar amount of "R" present per mole of $(EL_wAl_xP_ySi_z)O_2$ and has a value from zero to about 0.3; and "w", "x", "y" and "z" represent the mole fractins of $ELO_2^n$, $AlO_2^-$, $PO_2^+$, $SiO_2$, respectively, present as framework oxide units. "EL" is characterized as an element having (a) a mean "T—O" distance in tetrahedral oxide structures between about 1.51 Å and about 2.06 Å, (b) a cation electronegativity between about 125 kcal/g-atom to about 310 kcal/gm-atom and (c) a capability of forming stable M—O—P, M—O—Al or M—O—M bonds in crystalline three dimensional oxide structures having a "m-O" bond dissociation energy greater than about 59 kcal/g-atom at 298° K. "w", "x", "y" and "z" represent the mole fractions of "EL", aluminum, phosphorus and silicon, respectively, present as framework oxides. The mole fractions are within the limiting composition values or points as follows:

| Point | Mole Fraction | | |
|---|---|---|---|
| | x | y | (z + w) |
| A | 0.60 | 0.39–(0.01p) | 0.01(p + 1) |
| B | 0.39–(0.01p) | 0.60 | 0.01(P + 1) |
| C | 0.01 | 0.60 | 0.39 |
| D | 0.01 | 0.01 | 0.98 |
| E | 0.60 | 0.01 | 0.39 | where "p" is an integer corresponding to the number of elements which "EL" represents in the $(EL_wAl_xP_ySi_z)O_2$ composition.

The "EL" of the "ELAPSO" molecular sieves may be defined as representing at least one element capable of forming a framework tetrahedral oxide and is preferably selected from the group consisting of arsenic, beryllium, boron, chromium, cobalt, gallium, germanium, iron, lithium, magnesium, manganese, titanium and zinc and "w", "x", "y" and "z" represent the mole fractions of "EL", aluminum, phosphorus and silicon, respectively, present at tetrahedral oxides in which the mole fractions are within the limiting compositional values or points as follows:

| Point | Mole Fraction | | |
|---|---|---|---|
| | x | y | (z + w) |
| a | 0.60 | 0.39–(0.01p) | 0.01(p + 1) |
| b | 0.39–(0.01p) | 0.60 | 0.01(p + 1) |
| c | 0.10 | 0.55 | 0.35 |
| d | 0.55 | 0.10 | 0.35 | where "p" is as above defined.

The EP publication at page 16 discloses the use of crystalline and amorphous aluminophosphate as a source of phosphorus and aluminum and at page 17 describes seeding the reaction mixture. Examples 11A, 12A, 93A–103A, 5B, 6B, 55B, 58B, 59B, 50D–56D, 59D–62D and 12F–15F depict the use of seed crystals.

U.S. Pat. No. 4,500,651, patented Feb. 19, 1985

TAPO molecular sieves comprise three-dimensional microporous crystalline framework structures of [TiO$_2$], [AlO$_2$] and [PO$_2$] tetrahedral units which have a unit empirical formula on an anhydrous basis of:

$$mR:(Ti_xAl_yP_z)O_2 \qquad (1)$$

wherein "R" represents at least one organic templating agent present in the intracrystalline pore system; "m" represents the moles of "R" present per mole of (Ti$_x$Al$_y$P$_z$)O$_2$ and has a value of from zero to 5.0, the maximum value in each case depending upon the molecular dimensions of the templating agent and the available void volume of the pore system of the particular titanium molecular sieve; "x", "y" and "z" represent the mole fractions of titanium, aluminum and phosphorus, respectively, present as tetrahedral oxides, representing the following values for "x", "y" and "z":

| Point | Mole Fraction | | |
|---|---|---|---|
| | x | y | (z + w) |
| A | 0.001 | 0.45 | 0.549 |
| B | 0.88 | 0.01 | 0.11 |
| C | 0.98 | 0.01 | 0.01 |
| D | 0.29 | 0.70 | 0.01 |
| E | 0.0001 | 0.70 | 0.299 |

The parameters "x", "y" and "z" are preferably within the following values for "x", "y" and "z":

| Point | Mole Fraction | | |
|---|---|---|---|
| | x | y | (z + w) |
| a | 0.002 | 0.499 | 0.499 |
| b | 0.20 | 0.40 | 0.40 |
| c | 0.20 | 0.50 | 0.30 |
| d | 0.10 | 0.60 | 0.30 |
| e | 0.002 | 0.60 | 0.398 |

The TAPO molecular sieves are generally further characterized by an intracrystalline adsorption capacity for water at 4.6 torr and about 24° C., of about 3.0 weight percent. The adsorption of water has been observed to be completely reversible while retaining the same essential framework topology in both the hydrated and dehydrated state.

The U.S. patent at column 8, lines 65-68, and column 9, lines 15-18, discusses the use of crystalline amorphous aluminophosphate as a source of phosphorus and aluminum. At column 6, lines 1-5, seeding is described as facilitating the crystallization procedure. Comparative example 44 describes a composition of amorphous TiO$_2$ and 95 wt. % AlPO$_4$18 without an indication of how the composition was prepared.

U.S. Ser. No. 600,179, filed Apr. 13, 1984 now U.S. Pat. No. 4,684,617, EPC Publication 0 161 488, published Nov. 21, 1985

The TiAPSO molecular sieves have three-dimensional microporous framework structures of TiO$_2$, AlO$_2^-$, PO$_2^+$ and SiO$_2$ tetrahedral oxide units having an empirical chemical composition on an anhydrous basis expressed by the formula:

$$mR:(Ti_wAl_xP_ySi_z)O_2$$

wherein "R" represents at least one organic templating agent present in the intracrystalline pore system; "m" represents the molar amount of "R" present per mole of (Ti$_w$Al$_x$P$_y$Si$_z$)O$_2$ and has a value of from zero to about 0.3; and "w", "x", "y" and "z" represent the mole fractions of titanium, aluminum, phosphorus and silicon, respectively, present as tetrahedral oxides and each has a value of at least 0.01. The mole fractions "w", "x", "y" and "z" are generally defined in respect to the ternary diagram of FIG. 1 of the applications as being within the following limiting compositional values or points:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a subclass of TiAPSO molecular sieves the values "w", "x", "y" and "z" in the above formula are within the tetragonal compositional area defined by points a, b, c and d of the ternary diagram by points a, b, c and d of the ternary diagram of FIG. 2 of the aplications, said points a, b, c and d representing the following values for "w", "x", "y" and "z":

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The publication, at page 13, describes the use of crystalline or amorphous aluminophosphate as a source of phosphorus and aluminum and, at page 14, points out that seeding the reaction mixture facilitates the crystallization procedure.

U.S. Pat. No. 4,554,143, patented Nov. 19, 1985

Ferroaluminophosphates (FAPO's) are disclosed in U.S. Pat. No. 4,554,143, incorporated herein by reference, and have a three-dimensional microporous crystal framework structure of AlO$_2$, FeO$_2$ and PO$_2$ tetrahedral units and have an essential empirical chemical composition, on an anhydrous basis, of:

$$mR:(Fe_xAl_yP_z)O_2$$

wherein "R" represents at least one organic templating agent present in the intracrystalline pore system; "m" represents the moles of "R" present per mole of (Fe$_x$Al$_y$P$_z$)O$_2$ and has a value of from zero to 0.3, the maximum value in each case depending upon the molecular dimension of the templating agent and the available void volume of the pore system of the particular ferroaluminophosphate involved; "x", "y" and "z" represent the mole fractions of iron, aluminum and phosphorus, respectively, present as tetrahedral oxides, representing the following values for "x", "y" and "z":

| Point | Mole Fraction | | |
|---|---|---|---|
| | x | y | (z + w) |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the ferroaluminophosphates the values of "x", "y" and "z" in the formula above are representing the following values of "x", "y" and "z":

| Point | Mole Fraction | | |
|---|---|---|---|
| | x | y | (z + w) |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The iron of the $FeO_2$ structural units can be in either the ferric or ferrous valence state, depending largely upon the source of the iron in the synthesis gel. Thus, a $FeO_2$ tetrahedron in the structure can have a net charge of either $-1$ or $-2$.

The patent indicates at column 5, lines 43–45 and 54–56, that crystalline amorphous aluminophosphate may be used as a source of phosphorus and aluminum and at column 6, lines 1–5, describes seeding of the reaction mixture as facilitating the crystallization procedure.

U.S. application Ser. No. 600,173, filed Apr. 13, 1984 now U.S. Pat. No. 4,683,217, EPC Publication 0 161 491, published Nov. 21, 1985

The FeAPSO molecular sieves have a three-dimensional microporous crystal framework structures of $FeO_2^{-2}$ (and/or $FeO_2$), $AlO_2$, $PO_2$ and $SiO_2$ tetrahedral oxide units and having a unit empirical formula, on an anhydrous basis, of:

$$mR:(Fe_wAl_xP_ySi_z)O_2 \quad (1)$$

wherein "R" represents at least one organic templating agent present in the intracrystalline pore system; "m" represents the moles of "R" present per mole of $(Fe_wAl_xP_ySi_z)O_2$ and has a value of from zero to about 0.3; the maximum value of "m" in each case depends upon the molecular dimensions of the templating agent and the available void volume of the pore system of the particular molecular sieve involved; and "w", "x", "y" and "z" represent the mole fractions of iron, aluminum, phosphorus and silicon, respectively, present as tetrahedral oxides, said mole fractions being such that they are within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The EP publication, at page 12, describes the use of seeding the reaction mixture to facilitate the crystallization procedure. At page 18, the publication describes the use of crystalline amorphous aluminophosphates as a source of phosphorus and aluminum in making the molecular sieve.

U.S. Ser. No. 600,170, EPC Publication 0 158 975, published Oct. 23, 1985

The ZnAPSO molecular sieves of U.S. Ser. No. 600,170, filed Apr. 13, 1984 comprise framework structures of $ZnO_2^{-2}$, $AlO_2^-$, $PO_2^+$ and $SiO_2$ tetrahedral units havings an empirical chemical composition on an anhydrous basis expressed by the formula:

$$mR:(Zn_wAl_xP_ySi_z)O_2$$

wherein "R" represents at least one organic templating agent present in the intracrystalline pore system; "m" represents the molar amount of "R" present per mole of $(Zn_wAl_xP_ySi_z)O_2$ and has a value of zero to about 0.3; and "w", "x", "y" and "z" represent the mole fractions of zinc, aluminum, phosphorus and silicon, respectively, present as tetrahedral oxides and each has a value of at least 0.01. The mole fractions "w", "x", "y" and "z" are generally defined being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of ZnAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

This publication at page 13 discloses that crystalline or amorphous aluminophosphate may be used as a source of phosphorus or aluminum and at page 14 indicates that seeding of the reaction mixture with said crystals facilitates the crystallization procedure. Examples 12–15 are stated to employ the seeding procedure.

U.S. application Ser. No. 600,180, filed Apr. 13, 1984 now U.S. Pat. No. 4,758,419, EPC Publication 0 158 348, published Oct. 16, 1985

The MgAPSO molecular sieves have three-dimensional microporous framework structures of $MgO_2^{-2}$, $AlO_2^-$, $PO_2^+$ and $SiO_2$ tetrahedral oxide units and have an empirical chemical composition on an anhydrous basis expressed by the formula:

$$mR:(Mg_wAl_xP_ySi_z)O_2$$

wherein "R" represents at least one organic templating agent present in the intracrystalline pore system; "m" represents the molar amount of "R" present per mole of $(Mg_wAl_xP_ySi_z)O_2$ and has a value from zero to about 0.3; and "w", "x", "y" and "z" represent the mole fractions of magnesium, aluminum, phosphorus and silicon, respectively, present as tetrahedral oxides and each preferably has a value of at least 0.01. The mole fractions "w", "x", "y" and "z" are generally defined as being within the limiting compositional values or points as follows:

| Point | Mole Fraction | | |
|---|---|---|---|
|  | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

In a preferred subclass of the MgAPSO molecular sieves the values "w", "x", "y" and "z" in the above formula are within the limiting compositional values or points as follows:

| Point | Mole Fraction | | |
|---|---|---|---|
|  | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

This publication depicts seeding to generate product at page 14 and in examples 5, 6, 55, 58 and 59.

U.S. application Ser. No. 600,175, filed Apr. 4, 1984 now U.S. Pat. No. 4,686,092, EPC Publication 0 161 490, published Nov. 11, 1985

The MnAPSO molecular sieves of U.S. Ser. No. 600,175, filed Apr. 13, 1984 have a framework structure of $MnO_2^2$, $AlO_2$, $PO_2$, and $SiO_2$ tetrahedral units having an empirical chemical composition on an anhydrous basis expressed by the formula:

$$mR:(Mn_wAl_xP_ySi_z)O_2$$

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of element manganese, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
|  | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w., x, y and z may be as follows:

| Point | Mole Fraction | | |
|---|---|---|---|
|  | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The publication at page 13 describes the use of crystal or amorphous aluminophosphate as a source of phosphorus or aluminum, and at page 14 characterizes the use of said crystals to facilitate the crystallization procedure. Examples 54–56 and 59–62 state said crystals were used in the manufacture of the MnAPSO products.

U.S. application Ser. No. 600,174, filed Apr. 13, 1984 now U.S. Pat. No. 4,744,970, EPC Publication 0 161 489, published Nov. 21, 1985

The CoAPSO molecular sieves of U.S. Ser. No. 600,174, filed Apr. 13, 1984 have three-dimensional microporous framework structures of $CoO_2^2$, $AlO_2$, $PO_2$ and $SiO_2$ tetrahedral units and have an empirical chemical composition on an anhydrous basis expressed by the formula:

$$mR:(Co_wAl_xP_ySi_z)O_2$$

wherein "R" represents at least one organic templating agent present in the intracrystalline pore system; "m" represents the molar amount of "R" present per mole of $(Co_wAl_xP_ySi_z)O_2$ and has a value of from zero to about 0.3; and "w", "x", "y" and "z" represents the mole fractions of cobalt, aluminum, phosphorus and silicon, respectively, present as tetrahedral oxides, where the mole fractions "w", "x", "y" and "z" are each at least 0.01 and are generally defined, as being within the limiting compositional values or points as follows:

| Point | Mole Fraction | | |
|---|---|---|---|
|  | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the CoAPSO molecular sieves the values of "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The EP publication at page 13 depicts the use of crystalline amorphous aluminophosphate as a source of phosphorus and aluminum and at page 14 states that seeding the reaction mixture facilitates the crystallization procedure. Examples 11, 12, 13, 93 and 97–103 depict the use of seed crystals.

U.S. Ser. Nos. 599,771 now abandoned, 599,776 now abandoned, 599,807 now abandoned, 599,809 now abandoned, 599,811 now abandoned, 599,812 now abandoned, 599,813 now abandoned, 600,166 now abandoned, 600,171 now U.S. Pat. No. 4,686,093, each filed Apr. 13, 1984, EPC Publication 0 158 976, published Oct. 23, 1985

MeAPO molecular sieves are crystalline microporous aluminophosphates in which the substituent metal is one of a mixture of two or more divalent metals of the group magnesium, manganese, zinc and cobalt and are disclosed in U.S. Pat. No. 4,567,028. Members of this novel class of compositions have a three-dimensional microporous crystal framework structure of $MO_2^2$, $AlO_2$ and $PO_2$ tetrahedral units and have the essentially empirical chemical composition, on an anhydrous basis, of:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved; "x", "y" and "z" represent the mole fractions of the metal "M", (i.e., magnesium, manganese, zinc and cobalt), aluminum and phosphorus, respectively, present as tetrahedral oxides, said mole fractions being such that they are representing the following values for "x", "y" and "z":

| Point | Mole Fraction | | |
|---|---|---|---|
| | x | y | (z + w) |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the metal aluminophosphates of this invention, the values of "x", "y" and "z" in the formula above are representing the following values for "x", "y" and "z":

| Point | Mole Fraction | | |
|---|---|---|---|
| | x | y | (z + w) |
| a | 0.01 | 0.52 | 0.47 |
| b | 0.01 | 0.39 | 0.60 |
| c | 0.25 | 0.15 | 0.60 |

| Point | Mole Fraction | | |
|---|---|---|---|
| | x | y | (z + w) |
| d | 0.25 | 0.40 | 0.35 |

The as-synthesized compositions are capable of withstanding 350° C. calcination in air for extended periods, i.e., at least 2 hours, without becoming amorphous.

The EP publication at pages 14 and 15 depicts the use of crystalline and amorphous aluminophosphate as a source of phosphorus and aluminum and at page 15 states that seeding the reaction mixture facilitates the crystallization procedure. Example 8 discloses seeding of crystals.

EPC Applic. 85104386.9, filed Apr. 11, 1985 (EPC Publication No. 0158976, published Oct. 13, 1985) and
EPC Applic. 85104388.5, filed Apr. 11, 1985 (EPC Publication No. 158348, published Oct. 16, 1985)

"ELAPO" molecular sieves are a class of crystalline molecular sieves in which at least one element capable of forming a three-dimensional microporous framework form crystal framework structures of $AlO_2$, $PO_2$ and $MO_2$ tetrahedral oxide units wherein "$MO_2$" represents at least one different element (other than Al or P) present as tetrahedral oxide units "$MO_2$" with charge "n" where "n" may be −3, −2, −1, 0 or +1. The members of this novel class of molecular sieve compositions have crystal framework structures of $AlO_2$, $PO_2$ amd $MO_2$ tetrahedral units and have an empirical chemical composition on an anhydrous basis expressed by the formula:

$$mR:(M_xAl_yP_z)O_2$$

wherein "R" represents at least one organic templating agent present in the intracrystalline pore system; "m" represents the molar amount of "R" present per mole of $(M_xAl_yP_z)O_2$; "M" represents at least one element capable of forming framework tetrahedral oxides; and "x", "y" and "z" represent the mole fractions of "M", aluminum and phosphorus, respectively, present as tetrahedral oxides. "M" is at least one different elements ($M_1$) such that the molecular sieves contain at least one framework tetrahedral units in addition to $AlO_2$ and $PO_2$. "M" is at least one element selected from the group consisting of arsenic, beryllium, boron, chromium, gallium, germanium and lithium, and when "M" denotes two elements the second element may be one of the aforementioned and/or is at least one element selected from the group consisting of cobalt, iron, magnesium, manganese, titanium and zinc.

The ELAPO molecular sieves are generally referred to herein by the acronym or "ELAPO" to designate element(s) "M" in a framework of $AlO_2$, $PO_2$ and $MO_2$ tetrahedral oxide units. Actual class members will be identified by replacing the "EL" of the acronym with the elements present as $MO_2$ tetrahedral units.

When "M" denotes two elements "M" may also be at least one element selected from the group consisting of cobalt, iron, magnesium, manganese, titanium and zinc. For example, in each instance "M" includes at least one of the first group of elements, e.g., As, Be, etc., and when two or more elements are present, the second and further elements may be selected from the first group of elements and/or the second group of elements, as above discussed.

The ELAPO molecular sieves have crystalline three-dimensional microporous framework structures of $AlO_2$, $PO_2$ and $MO_2$ tetrahedral units and have an empirical chemical composition on an anhydrous basis expressed by the formula:

$$mR:(M_xAl_yP_z)O_2;$$

wherein "R" represents at least one organic templating agent present in the intracrystalline pore system; "m" represents the molar amount of "R" present per mole of $(M_xAl_yP_z)O_2$ and has a value of zero to about 0.3; "M" represents at least one element capable of forming framework tetrahedral oxides where "M" is at least one element selected from the group consisting of arsenic, beryllium, boron, chromium, gallium, germanium and lithium. When "M" includes an additional element such additional elements "M" may be at least one element selected from the group consisting of cobalt, iron, magnesium, manganese, titanium, and zinc.

The relative amounts of element(s) "M", aluminum and phosphorus are expressed by the empirical chemical formula (anhydrous):

$$mR:(M_xAl_yP_z)O_2$$

where "x", "y" and "z" reprresent the mole fractions of said "M", aluminum and phosphorus. The individual mole fractions of each "M" (of when M denotes two or more elements, $M_1$, $M_2$, $M_3$, etc.) may be represented by "$x_1$", "$x_2$", "$x_3$", etc. wherein "$x_1$", "$x_2$", and "$x_3$", and etc. represent the individual mole fractions of elements $M_1$, $M_2$, $M_3$, and etc. for "M" as above defined. The values of "$x_1$", "$x_2$", "$x_3$", etc. are as defined for "x" hereinafter, where "$x_1$"+"$x_2$"+"$x_3$"... ="x" and where $x_1$, $x_2$, $x_3$, etc. are each at least 0.01.

The ELAPO molecular sieves have crystalline three-dimensional microporous framework structures of $MO_2$, $AlO_2$ and $PO_2$ tetrahedral units having an empirical chemical composition on an anhydrous basis expressed by the formula:

$$mR:(M_xAl_yP_z)O_2$$

wherein "R" represents at least one organic templating agent present in the intracrystalline pore system; "m" represents a molar amount of "R" present per mole of $(M_xAl_yP_z)O_2$ and has a value of zero to about 0.3; "M" represents at least one different element (other than Al or P) capable of forming framework tetrahedral oxides, as hereinbefore defined, and "x", "y" and "z" represent the mole fractions of "M", aluminum and phosphorus, respectively, present as tetrahedral oxides; said mole fractions "x", "y" and "z" being generally defined as within the following values for "x", "y", and "z":

| Point | Mole Fraction | | |
|-------|------|------|--------|
|       | x    | y    | (z + w) |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred sub-class of the ELAPOs of this invention, the values of "x", "y" and "z" in the formula above are within the following values for "x", "y" and "z":

| Point | Mole Fraction | | |
|-------|------|------|--------|
|       | x    | y    | (z + w) |
| a | 0.02 | 0.60 | 0.39 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

U.S. Pat. No. 4,310,440

ALPO's are the basic and simplest of the crystalline aluminophosphates. They each having a framework structure whose chemical composition expressed in terms of mole ratios of oxides is:

$$Al_2O_3:1.0\pm0.2\ P_2O_5:$$

each of said framework structures being microporous in which the pores are uniform and have nominal diameters within the range of about 3 to about 10Å, an intracrystalline adsorption capacity for water at 4.6 torr and 24° C. of at least 3.5 weight percent, the adsorption and desorption of water being completely reversible while retaining the same essential framework topology in both the hydrated and dehydrated state.

U.S. Pat. Applications 600,168 now abandoned, 600,181 now U.S. Pat. No. 4,741,892, 600,182 now abandoned, 600,183 pending, European Patent Publ. 0 158 350, publ. Oct. 16, 1985

SENAPSO are quinary and senary molecular sieves that have framework structures of at least two elements having tetrahedral oxide units "$MO_2^n$" and having $AlO_2^-$, $PO_2^+$ $SiO_2$ tetrahedral oxide units, where "n" is $-3$, $-2$, $-1$, 0 or $+1$, and have an empirical chemical composition on an anhydrous basis expressed by the formula:

$$mR:(M_wAl_xP_ySi_z)O_2$$

wherein "R" represents at least one organic templating agent present in the intracrystalline pore system; "m" represents the molar amount of "R" present per mole of $(M_wAl_xP_ySi_z)O_2$ and has a value of from 0 to about 0.3; "M" represents at least two elements selected from the group consisting of arsenic, beryllium, boron, chromium, cobalt, gallium, germanium, iron, lithium, magnesium, manganese, titanium, vanadium, and zinc; "n" is as above defined; and "w", "x", "y" and "z" represent the mole fractions of elements "M", aluminium, phosphorus and silicon, respectively, present as tetrahedral oxides, each having a value of at least 0,01.

The publication, at pages 14–15, generally describes seeding reaction mixtures to form the desired product.

Zeolitic molecular sieves may be represented by the general formula:

$$Me_{\frac{x}{n}}[(AlO_2)_x(SiO_2)_y].zH_2O$$

where Me is a metal cation, x/n is the number of exchangeable metal cations of valence n, x is also the number of aluminum ions combined in the form of aluminate, y is the number of silicon atoms and z is the number of water molecules, removal of which produces the characteristic pore or channel system. The ratio z/x is a number from 1 to 5, usually from 1 to 2.

Typical of the zeolitic molecular sieves are chabazite, faujasite levynite, Linde Type A, gismodine, erionite, sodalite, Linde Type X and Y, analcime, gmelinite, harmotome, levynite, mordenite, epistilbite, heulandite, stilbite, edingtonite, mesolite, natrolite, scolecite, thomsonite, brewsterite, laumontite, phillipsite, the ZSM's (e.g., ZSM-5[2], ZSM-20[3], ZSM-12[4], ZSM-34[5], etc.) and Beta[6] and the like. Typical of suitable zeolitic molecular sieves employable in the practice of this invention are the following:

Zeolites- A, AgX, AgY, AlHY, alkylammonium X and Y, BAX, BaY, BeY, Ca-A, Ca-near faujasite, Ca-HX, Ca-X, Ca-Y, CdX, CdY, CeY, CoA, CoX, CoY, CrY, CsL, CsX, CsY, Cu-X, Cu-Y, Cu-diethylammonium Y, Cu-ethylammonium Y, Fe-X, Fe-Y, group IAX, group IAY, group IIAY, HY, KL, KX, KY, L, La-X, La-Y, LiA, LiX, LiY, LZ-10, LZ-210, MgHY, MgNa, MgNH$_4$Y, MgX, MgY, MnX, MnY, Na-A, Na-near faujasite, Na-L, Na-X, Na-Y, NH$_4$L, NH$_4$X, NH$_4$Y, Ni-A, Ni-X, Ni-Y, omega, PdY, phosphate, Pt, rare earth X, rare earth Y, RbX, RhY, SrX, SrY, steam stabilized or ultra stable Y, tetramethylammonium Y, TlX, triethylammonium Y, X, Y, Y-82, ZK-5, Zn-mordenite, Zn-X, An-Y, the ZSMs, supra, and the like.

[2] See U.S. Pat. No. 3,207,886.
[3] See U.S. Pat. No. 3,972,983.
[4] See U.S. Pat. No. 3,832,449
[5] See U.S. Pat. No. 4,079,095.
[6] See U.S. Pat. No. 3,308,069 and U.S. Reissue Patent No. 28,341.

Other zeolitic CMSCs useful in the present invention include boron-treated aluminosilicates, such as described in U.S. Pat. No. 4,613,720. Other NZMSs include the silica molecular sieves, such as silicalite as depicted in U.S. Pat. No. 4,061,724.

The average diameter of the pores on the presently useful CMSMs is preferably in the range of about 3 angstroms to about 15 angstroms as determined by measurements described in "Zeolite Molecular Sieves" by Donald W. Breck, published by John Wiley & Sons, New York, 1974. This average diameter is referred to as the average effective diameter. When the feedstock and desired product or products are relatively small, e.g., organic components containing 1 to about 10 and preferably 1 to about 4 carbon atoms per molecule, the CMSC preferably has small pores. The presently useful small pore CMSC's are defined as having pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane and more preferably by adsorption of n-hexane (average kinetic diameter of about 0.43 nm) and negligible adsorption of isobutane. Negligible adsorption of a given adsorbate is adsorption of less than three percent by weight of the CMSC and adsorption of the adsorbate is over three percent by weight of the adsorbate based on the weight of the CMSC. Certain of the CMSCs useful on the present invention have pores with an average effective diameter in the range of about 3 angstroms to about 5 angstroms.

The presently useful CMSCs may be incorporated into a solid composition, preferably solid particles, in which the catalyst is present in an amount effective to promote the desired chemical conversion. In one embodiment, the solid particles comprise a catalytically effective amount of the catalyst and matrix material, preferably at least one of a filler material and a binder material, to provide a desired property or properties, e.g., desired catalyst dilution, mechanical strength and the like, to the solid composition. Such matrix materials are often to some extent porous in nature and often have some nonselective catalytic activity to promote the formation of undesired products and may or may not be effective to promote the desired chemical conversion. For example, acid sites in the matrix material may promote non-selective chemical conversion. Such matrix, e.g., filler and binder, materials include, for example, synthetic and naturally occurring substances, metal oxides, clays, silicas, aluminas, silica-aluminas, silica-magnesias, silica-zirconias, silica-thorias, silica-berylias, silica-titanias, silica-alumina-thorias, silica-aluminazirconias, mixtures of these and the like.

The solid composition, e.g., solid particles, preferably comprises about 1% to about 99%, more preferably about 5% to about 90% and still more preferably about 10% to about 80%, by weight of CMSC; and about 1% to about 99%, more preferably about 5% to about 90% and still more preferably about 10% to about 80%, by weight of matrix material.

The preparation of solid compositions, e.g., solid particles, comprising CMSC and matrix material, is conventional and well known in the art and, therefore, need not be discussed in detail here. Certain of such preparation procedures are described in the patents and patent applications previously incorporated by reference herein, as well as in U.S. Pat. Nos. 3,140,253 and Re. 27,639. Catalysts which are formed during and/or as part of the methods of manufacturing the solid compositions are within the scope of the present invention.

In one embodiment, at least one component of the solid composition, preferably at least a portion of the matrix material component, is contacted prior to the feedstock/solid composition contacting to provide a more effective solid composition. In a particular embodiment, at least a portion of the matrix material (or matrix material precursor) is contacted prior to the matrix material being combined in the solid composition. For example, if the matrix material includes acid sites which can result in non-selective chemical conversion during the feedstock/solid composition contacting, the matrix material, preferably separate and apart, from the CMSC, can be contacted with a basic component, e.g., ammonia and the like, in an amount effective to neutralize at least a portion, preferably a major portion and more preferably substantially all, of the acid sites on the matrix material being contacted. Care should be taken to avoid regenerating these acid sites. After this contacting, the matrix material and CMSC can be combined into the solid composition, e.g., using conventional techniques.

This embodiment provides substantial advantages. For example, the matrix material alone may be contacted at more severe conditions than would be possible if the CMSC was present. Also, relatively inexpensive basic components, e.g., ammonia and the like, can be employed to contact the matrix material, again with no concern for harming the CMSC which is not present. Of course, this contacting should be conducted so as not to substantially adversely affect the matrix material being contacted, the final composition or the desired chemical conversion.

The solid particles including the CMSC may be of any size functionally suitable in the present invention. In order that the catalyst can be utilized more effectively and if a fixed bed of solid particles is not employed, the solid particles are preferably small relative to fixed bed solid particles used to promote similar chemical conversions. More preferably, the solid particles have a maximum transverse dimension, e.g., diameter, in the range of about 1 micron to about 500 microns, still more preferably about 25 microns to about 200 microns.

The solid particles may be subjected to spray drying as part of the solid particle manufacturing process to form the solid particles or precursors of the solid particles. An additional advantage of employing such spray drying is that the conditions of such step can be controlled so that the product solid particles are of a desired particle size or size range. The use of spray drying in such solid particle manufacturing is conventional and well known, and therefore need not be discussed in detail here.

The non-zeolitic molecular sieves or NZMSs are particularly useful in the practice of the present invention. Among the NZMSs, the SAPOs are particularly useful. SAPO-17 and SAPO-34, which is described in detail in Example 36 of U.S. Pat. No. 4,440,871, are especially preferred catalysts for promoting the reaction of molecules containing one carbon atom, e.g., methane, methanol, methyl halide, and the like, to form products containing up to about 6, preferably up to about 4, carbon atoms per molecule, e.g., ethylene, propylene, butylene and the like. Currently, SAPO-34 is most preferred.

Although the present process may be conducted in the presence of a solid particles/liquid slurry, it is preferred that the solid particles be present in the fluidized state or as a fixed bed, more preferably in the fluidized state, e.g., as a fluidized bed of solid particles. The use of fluidized solid particles provides improved process control, in particular temperature control and catalytic activity control and/or selectivity control to the desired product.

The chemical conversion or reaction obtained by practicing the present invention can vary widely and depends, for example, on the feedstock and catalyst employed and on the feedstock/catalyst contacting conditions used. Substantially any chemical conversion or reaction which is capable of being catalyzed by a CMSC and conducted in a slurry system may be conducted while practicing the present invention. Examples of reactions which may be obtained include cracking; disproportionation; olefin production from non-olefin feedstocks; olefin interconversion; aldol, e.g., aldehyde-aldehyde, ketone-ketone, aldehyde-ketone and aldehyde or ketone-aromatic component, condensation; condensation reactions to produce cyclic lactams; isoprene formation; alkylation (aromatic, e.g., benzene, toluene and phenol alkylation); and isomerization (xylene isomerization). One particularly referred chemical conversion or reaction involves olefin production from non-olefin feedstocks, more preferably feedstocks comprising aliphatic hetero compounds.

Substantially any feedstock or combination of feedstocks including 1 to about 6 carbon atoms per molecule may be employed in the present invention. The present reaction system is particularly applicable to organic feedstocks containing 1 to about 6 carbon atoms per molecule, preferably having molecules comprising carbon and hydrogen, and more preferably at least one other element. This other element is preferably selected from the group consisting of oxygen, sulfur, halogen, nitrogen, phosphorus and mixtures thereof, with oxygen being particularly preferred.

The present invention is particularly useful in converting feedstocks having relatively small molecules, i.e., molecules having relatively small kinetic diameters. Thus, the feedstock contains 1 to about 6, preferably 1 to about 4, carbon atoms per molecule. Aliphatic hetero compounds are particularly preferred feedstocks for use in the present invention, especially when light olefins, i.e., olefins containing 2 to about 6 and preferably 2 to 4 carbon atoms per molecule, are to be produced. When light olefins are the desired product, such olefins are preferably produced as the major hydrocarbon product, i.e. over 50 mole percent of the hydrocarbon product is light olefins. The term "aliphatic hetero compounds" is employed herein to include alcohols, halides, mercaptans, sulfides, amines, ethers and carbonyl compound (aldehydes, ketones, carboxylic acids and the like). The aliphatic moiety preferably contains from 1 to about 10 carbon atoms and more preferably contains from 1 to about 4 carbon atoms. Suitable reactants include lower straight or branched chain alkanols, their unsaturated counterparts, and the nitrogen, halogen and sulfur analogue of such. Representative of suitable aliphatic hetero compounds include: methanol; methyl mercaptan; methyl sulfide; methyl amine; dimethyl ether; ethanol; ethyl mercaptan; ethyl chloride; diethyl ether; methyethyl ether; formaldehyde; dimethyl ketone; acetic acid; n-alkyl amines; n-alkyl halides and n-alkyl sulfides having n-alkyl group having 3 to 6 carbon atoms; and mixtures thereof. In one embodiment, e.g., where light olefins are the desired products, the feedstock is preferably selected from the group consisting of methanol, ethanol, dimethyl ether, diethyl ether and mixtures thereof, with methanol being particularly preferred.

In certain instances, it is preferred that the feedstock/solid composition contacting conditions be such that the contacting temperature exceed the critical temperature of the feedstock. In other words, in certain embodiments, the feedstock is preferably in the supercritical state at the feedstock/solid composition contacting conditions. Having the feedstock in the supercritical state is particularly useful when the feedstock contains 1 to about 4 carbon atoms per molecule.

The product or products obtained from the feedstock/solid composition contacting will, of course, depend, for example, on the feedstock, catalyst and conditions employed. Preferably, the desired product is organic. However, it should be noted that a necessary, and therefore desired, reaction byproduct may be inorganic even when the primary product sought is organic. This is exemplified by the conversion of methanol to light olefins plus water. The organic product or products have molecules which preferably include carbon and hydrogen. In one embodiment, the desired product preferably contains 1 to about 6, more preferably 1 to about 4, carbon atoms per molecule. The desired product or products preferably have kinetic diameters which allow such product or products to be removed from or escape from the pores of the CMSC.

In addition to the feedstock, a diluent may be used in conjunction with the feedstock if desired and/or beneficial to the overall process. Such diluent may be mixed or combined with the feedstock prior to the feedstock/solid composition contacting or it may be introduced into the reaction zone separately from the feedstock. Preferably, the feedstock and diluent are both substantially continuously fed to the reaction zone during this contacting. Such diluent preferably acts to moderate the rate, and possibly also the extent, of feedstock chemical conversion and may also act to aid in temperature control.

Typical of the diluents which may be employed in the instant process are helium, argon, nitrogen, carbon monoxide, carbon dioxide, hydrogen, water, hydrocarbons and mixtures thereof. The diluent, if any, is preferably selected from the group consisting of helium, argon, nitrogen, carbon monoxide, carbon dioxide, hydrogen, water and mixtures thereof, with water, nitrogen and mixtures thereof, in particular water, being more preferred. The amount of diluent employed, if any, may vary over a wide range depending on the particular application involved. For example, the amount of diluent may be in an amount in the range of about 0.1% or less to about 99% or more of the moles of feedstock.

The feedstock/solid composition contacting step of the present process often results in the CMSC losing at least a portion of at least one desirable property, e.g., catalytic property. The solid composition is preferably contacted with regeneration medium to substantially maintain or improve the effectiveness of the catalyst to promote the desired chemical conversion. For example, the catalyst may become less effective due to formation of carbonaceous deposits or precursors of such deposits in the pores or other parts of the CMSC and/or solid composition during the feedstock/solid composition contacting. In one embodiment, the regeneration medium acts to reduce the average kinetic diameter of molecules present on the pores of the CMSC. Such reduction in the kinetic diameter of these molecules is preferably sufficient to allow the resulting molecules to leave or exit the catalyst pores, thereby providing more pores and/or pore volume for the desired chemical conversion. The catalyst is regenerated, such as for example, by removing carbonaceous deposit material by oxidation in an oxygen-containing atmosphere.

In one embodiment, the catalyst and/or solid composition, preferably the catalyst, includes at least one added component effective to promote the action of the regeneration medium. For example, the catalyst may include at least one metal component effective to promote the oxidation of the carbonaceous deposit material. Of course, such metal component should have no substantial adverse effect on the desired chemical conversion. The specific added catalyst component depends on the requirement of the particular application involved. Examples of such added components include components of transition metals, such as nickel, cobalt, iron, manganese, copper and the like; the platinum group metals such as platinum, palladium, rhodium and the like; and the rare earth metals such as cerium, lanthanum and the like, and mixtures thereof. If an added metal component is used, it is preferred that this component be present as a minor amount, more preferably as about 1 ppm to about 20%, by weight (calculated as elemental metal) of the weight of catalyst employed.

Alternately to the oxidative catalyst regeneration, a reducing medium can be employed to regenerate the catalyst. Such reducing medium, preferably selected from the group consisting of hydrogen, carbon monoxide and mixtures thereof, and in particular hydrogen, can, for example, be used to react with molecules, e.g., of carbonaceous deposit material precursor, in the pores of the catalyst to produce molecules of reduced kinetic diameter so that such produced molecules can exit the pores of the catalyst. In one embodiment, the reducing medium is hydrogen and the catalyst includes at least one component, preferably a metal component, effective to promote hydrogenation of molecules present on the catalyst, e.g., in the pores of the catalyst, at the conditions of the reductive regeneration.

In one embodiment the regenerated solid composition, prior to being used again in the feedstock/solid composition contacting step is subjected to one or more treatments or contactings to condition the regenerated solid composition to have increased effectiveness, e.g., increased selectivity to the desired product or products, in the feedstock/solid composition contacting step. For example, the regenerated solid composition can be contacted at an increased temperature relative to the temperature at which the solid composition/regeneration medium contacting takes place and/or in the presence of steam (in the substantial absence of feedstock) in an amount effective to condition the regenerated solid composition to have increased effectiveness in the feedstock/solid composition contacting. The amount of steam employed during this contacting is preferably increased relative to the steam, if any, conventionally used to transfer such solid composition or solid particles from a catalyst regeneration zone to a reaction zone. In one particular embodiment where steam is used as a diluent in the feedstock/solid composition contacting step, the diluent steam is contacted preferably at a temperature increased relative to the regeneration temperature, with the solid composition prior to the feedstock/solid composition contacting to condition the solid particles as described herein. Such high temperature/steam contacting often deactivates the solid composition, in particular the matrix material of the solid composition, to some extent and acts to improve the selectivity of the solid composition to the desired product or products. Preferably both high temperatures and steam are employed. Care should be taken to control this contacting to avoid substantial permanent or irreversible damage to the CMSC.

In one embodiment, the regenerated solid composition is contacted in the presence of at least one component in an amount effective to condition the regenerated solid composition to have increased effectiveness in the feedstock/solid composition contacting. The component may be inorganic or organic, with organic components being preferred. Such organic components preferably include carbon and hydrogen, and more preferably at least one other element, for example, halogen, nitrogen, oxygen, phosphorus, sulfur and mixtures thereof. Preferably, the component is substantially incapable of entering the pores of the CMSC. For example, the component may be dibenzyl benzenes, diphenyl ether and the like and mixtures thereof, particularly if the CMSC has pores with small average effective diameters, i.e., about 5 angstroms or less.

In a particular embodiment, this component is a basic component, more preferably a basic component the molecules of which are substantially prevented, e.g., because of size and/or shape considerations, from entering the pores of the CMSC. Such basic component preferably acts to inactivate or reduce the undesired catalytic activity of the matrix material without substantially affecting the desired catalytic activity of the CMSC. The basic material is preferably selected from the group consisting of pyridine, pyridine derivatives, quinoline, quinoline derivatives and mixtures thereof, particularly when the preferred relatively small effective diameter CMSCs are employed. The amount of such basic components or components employed may vary over a wide range, provided that such component is effective to improve the effectiveness of the solid composition. Such basic component is preferably present in an amount in the range of about 0.1% to about 20%, more preferably about 0.1% to about 15%, by weight of the solid composition.

In another embodiment, the regenerated solid composition is contacted with a feed material, preferably other than the feedstock or the product, at conditions to chemically convert the feed material and condition the regenerated solid composition to have increased effectiveness in the feedstock/solid composition contacting. The chemical conversion of such feed material preferably selectively deactivates the matrix material in the regenerated solid composition. This feed material/solid composition contacting preferably takes place in the substantial absence of the feedstock and the desired product. The feed material, and the product or products of the conversion of the feed material and the feed material/regenerated solid composition contacting conditions should have no substantial detrimental effect on the CMSC, the feedstock and desired product and on the feedstock/solid composition contacting. The feed material is preferably selected to be substantially incapable of entering the pores of the CMSC. One particularly preferred class of feed materials is hydrocarbons, more preferably paraffins. The hydrocarbons employed preferably contain about 3 to about 20, more preferably about 7 to about 20, carbon atoms per molecule. Preferably, the feed material/regenerated solid composition contacting takes place at conditions effective to form carbonaceous deposit material, or precursors of such deposit material, on the solid composition. More preferably, the regenerated solid composition after this feed material/regenerated solid composition contacting contains about 0.5% to about 20% by weight of such deposit material and/or precursors of such deposit material. In one specific embodiment, the feed material/regenerated solid composition contacting occurs at conditions to crack the hydrocarbons, e.g., paraffins. Such conditions preferably include temperatures in the range of about 20° C. to about 600° C.

The above-noted embodiments involving subjecting the regenerated solid composition to one or more treatments or contactings to condition the regenerated solid composition to have increased effectiveness in the feedstock/solid composition contacting step can be advantageously utilized to contact the unused or virgin solid composition prior to the initial feedstock/solid composition contacting. Thus, such treatments or contactings of unused or virgin solid composition to condition the solid composition to have increased effectiveness in the feedstock/solid composition contacting step are within the scope of the present invention.

The instant feedstock/solid composition contacting step may be carried out in a single reaction zone or a plurality of such zones arranged in series or in parallel.

After the desired product or products are separated from the solid composition using, for example, solid/gas separation devices such as cyclone separators, various techniques, such as distillation, adsorption and the like, can be used to recover or purify such product or products.

The conditions at which the feedstock/solid composition contacting occurs can vary widely depending, for example, on the specific feedstock and CMSC employed, and on the specific product or products desired. The present process is particularly applicable with feedstock/solid composition contacting temperatures in excess of about 200° C., more preferably in excess of about 300° C., and with pressures in excess of about 10 psig., more preferably in excess of about 50 psig. If light olefins are to be produced from feedstock containing 1 to about 4 carbon atoms per molecule, feedstock/solid composition contacting temperatures are preferably in the range of about 200° C. to about 600° C. or even about 700° C., more preferably about 350° C. to about 550° C. and still more preferably about 400° to about 500° C., with pressures preferably below about 1500 psig.

The following non-limiting examples are provided to better illustrate the invention.

EXAMPLES 1 TO 4

Two matrix materials, designated Matrix A and Matrix B, were conventionally spray dried into solid particles having an average particle size of about 150-200 microns. Matrix A was composed of 15% by weight of alumina binder and 85% by weight of kaolin clay filler. Matrix B was composed of 25% by weight of alumina binder and 75% by weight of kaolin clay filler.

An experimental apparatus used in Examples 1 to 4 was as follows:

The reactor was a 1 inch O.D. stainless steel fluidized bed reactor with an extended disengagement zone at the top. The reactor had previously been coated internally with sodium silicate to minimize the catalytic activity of the reactor itself. The reactor was loaded with either Matrix A or Matrix B, as desired. The reactor temperature was controlled by the Techne SBL2-D fluidized sand bath in which the reactor was located.

Analytical grade methanol was fed using a metering pump. The methanol was vaporized and preheated in the feed lines to the reactor using heat tape. Methanol flow was measured by periodically timing the level change in a burette on the pump suction line. A small rotameter was also used to check the methanol flow.

Nitrogen diluent was fed from high pressure cylinders. It was mixed with the methanol upstream of the reactor. When pyridine was fed to the reactor in place of methanol, nitrogen was also fed to the reactor in an amount and at a rate sufficient to maintain the matrix material in a fluidized state. Nitrogen flow was controlled with a Veriflow controller, and measured with a rotameter.

Pressure in the reactor was controlled using a Grove pressure regulator on the reactor outlet. Pressure was reduced after the reactor outlet to about 5 psig. to avoid condensation in the sample lines. From the reactor, steam jacketed lines led to the gas chromatograph, then to the turbine flow meter used for measuring gas flows. Fittings and other potentially cool areas were electrically heated and insulated to prevent any condensation of water or heavy products in the sample lines. The gas stream then went to a condenser, through a wet test meter and was vented back to a hood.

Regeneration was controlled by a set of low wattage ASCO solenoid switching valves, which were controlled by an IBM PC driven ISAAC data acquisition and control system.

A brief series of two (2) experiments was run at substantially constant temperature, pressure, and methanol and nitrogen feedrates. Approximately two (2) minutes into each experiment, the methanol feed to the reactor was stopped, pyridine was substituted for the methanol for a brief time, and then methanol (with no pyridine) was again fed to the reactor.

A second brief series of two (2) experiments was run repeating the first series except that a material comprising primarily diphenyl ether, and sold by Dow Chemical Company under the tradename Dowtherm A, was used instead of pyridine.

In each of the first experiments, the system was operated at conditions which would normally (without the substitution of pyridine) give long-term methanol conversion to products other than dimethyl ether of about 7 to 8%. Upon resuming methanol flow after pyridine contacting, methanol conversion immediately dropped to less than 3%. However, as the experiments continued, the methanol conversion gradually recovered to about the previous level. In the second series of experiments, treatment with the diphenyl ether material resulted in a drop in methanol conversion from about 5.6% to about 4.8%.

Without limiting the present invention to any theory or mechanism of operation, it may be is postulated that the pyridine was adsorbed on the surface of the matrix material. The pyridine was gradually desorbed during the experiments, exposing the active acid sites of the matrix material again. The relatively large, bulky diphenyl ether molecules are also adsorbed on, and desorbed from, the surface of the matrix material. The pyridine was more effective than the diphenyl ether in reducing the largely non-selective catalytic activity of the matrix materials because it is basic and can chemically neutralize the acid sites of the matrix material.

The use of such conditioning agents is particularly advantageous when a small pore CMSC is included in solid particles including such matrix materials. The molecules of the conditioning agent are sized, e.g., have kinetic diameters, such that the conditioning agent is substantially prevented from entering the pores of the CMSC. Thus, the conditioning agent effectively reduces the largely non-selective catalytic activity of the matrix material without substantially affecting the CMSC. Overall, the solid particles are more selective toward promoting the desired chemical conversion of the feedstock, e.g., methanol.

Since the matrix material is often most active at the start of feedstock contacting, it may be desirable to contact the solid particles with an effective amount of conditioning agent prior to such contacting. When the conditioned solid particles are contacted with the feedstock, the solid particles often gradually become deactivated. This gradual deactivation may continue to moderate the non-selective activity of the matrix material even though the conditioning agent may gradually become disassociated, e.g., desorbed, from the solid particles. In one embodiment, the conditioning agent is fed to the feedstock/solid particles contacting zone or zones, preferably on a substantially continuous basis during such contacting, to maintain a level, preferably a substantially steady-state level of conditioning agent associated, e.g., adsorbed, on the solid particles. Of course, the solid particles can be contacted with conditioning agent prior to the feedstock contacting, and also the conditioning agent can be fed to the feedstock/solid particle contacting zone. The specific conditioning agent employed and the amounts of agent to be employed and the optimum method of employing the conditioning agent are to be chosen based on the specific application to be encountered.

EXAMPLE 5

This Example illustrates an additional approach to improving the overall catalytic performance of solid particles comprising CMSC and matrix material.

A first slurry of 50% by weight SAPO-34 crystals and 50% by weight water is prepared and subjected to continuous mixing.

In a separate vessel, a second, aqueous slurry of kaolin clay and alumina is prepared. Ammonia gas is bubbled through this second slurry until substantially all the acid sites in both the alumina and kaolin clay are neutralized. The first slurry is added to the second slurry to form a combined slurry which is mixed for about 10 minutes. The combined slurry is then stone milled to obtain a substantially uniform particle distribution.

The milled slurry is then spray dried to produce particles having an average particle size of about 70 microns. The spray dried particles are calcined for two hours at 600° C. in a nitrogen atmosphere.

The compositions of the first and second slurries are chosen so that the final particles contained 60% by weight SAPO-34, 23% by weight kaolin clay and 17% by weight alumina.

These solid particles are tested for methanol conversion capacity in the apparatus described above. These solid particles have improved overall selectivity to light olefins relative to similar solid particles in which the matrix material is not contacted with ammonia.

This approach to modifying the performance of solid particles is advantageous because any suitable basic material may be employed. In other words, the CMSC is not present during the basic material/matrix material contacting, there is no need to choose the basic material not to interfere with the pores of the catalyst. Of course, the basic material chosen should have no substantially deleterious effect on the matrix material, the final solid particles or on the desired feedstock conversion. Also, care should be exercised to inhibit the regeneration of acid sites in the matrix material after such acid sites have been neutralized. In one embodiment, the solid particles prepared by neutralizing acid sites in the matrix material are advantageously contacted with one or more conditioning agents prior to and/or during the feedstock/solid particle contacting.

EXAMPLE 6

This Example illustrates a further additional approach to improving the overall catalytic performance of solid particles comprising CMSC and matrix material.

Solid particles produced in accordance with Example 5, except that no ammonia contacting is employed, are used. These particles are contacted with dodecane at conditions effective to crack a portion of the dodecane and form carbonaceous deposit material on the solid particles. This contacting is continued until the solid particles include about 2% by weight of the carbonaceous deposit material.

These carbonaceous deposit containing material-containing solid particles are tested for methanol conversion capability in the apparatus described above. These solid particles have improved overall selectivity to light olefins relative to similar solid particles which include no carbonaceous deposit material.

EXAMPLE 7

A commercially sized fluidized bed reaction system is constructed to produce 5000 barrels per day of mixed ethylene and propylene from methanol. The system includes three reactor vessels in parallel. Each of the reactor vessels are equipped with a number of cyclone separators to aid in removing gases from the reactor vessel while holding the catalyst inside. The system also includes a conventional product handling/separation subsystem to recover and purify the products to the extent desired.

The feed system to each of the reactor vessels includes a separate steam inlet. Steam is substantially continuously fed to each of the vessels. A valved methanol inlet and a valved air inlet are also provided to each of the vessels. The methanol and air inlets are controlled so that only one of methanol or air is fed to any one reactor vessel at any one time.

Each of these reactor vessels are operated on the following reaction/regeneration cycle. Solid particles, similar in composition to that prepared in Example 5, are placed in the reaction vessel and heated to a temperature of 500° C. Pyridine is combined with the steam and fed to the vessel for a time sufficient to neutralize a major portion of the acid sites in the matrix material of the solid particles. Vaporized and heated methanol is fed to the vessel (along with the pyridine and the steam diluent) to produce light olefins which are removed from the vessel through the cyclone separators. Throughout the cycle the catalyst is maintained at a temperature of about 500° C. and a pressure of about 80 psig. After a period of time, methanol flow and pyridine flow is stopped and steam purges the vessel of methanol. After the purge, air is introduced into the reactor vessel to regenerate the catalyst. After the desired catalyst regeneration, the flow of air is stopped and steam purges the vessel of air. At this point, the cycle is begun again. The time sequencing of this cyclic operation is such that no less than two of the reactor vessels operate in the reaction mode at any one time.

This cyclic operation is effective in producing ethylene and propylene, in particular ethylene, from methanol.

While the present invention has been described with respect to various specific examples and embodiments, it is to be understood that the invention is not limited thereto and that it can be variously practiced within the scope of the following claims.

What is claimed is:

1. In a process for converting a non-olefinic feedstock containing 1 to about 6 carbon atoms per molecule which includes the discrete sequential steps of (a) contacting said feedstock with a solid composition comprising a crystalline microporous three dimensional solid catalyst having the ability to promote said conversion, and matrix material at conditions effective to convert said feedstock, to produce a hydrocarbon product containing light olefins and to at least partially deactivate said solid composition; (b) contacting said deactivated solid composition with regeneration medium at conditions effective to at least partially regenerate said solid composition; and (c) repeating step (a), the improvement which comprises (d) conditioning said regenerated solid composition in the presence of at least one added conditioning agent comprising a basic material that is substantially incapable of entering the pores of said catalyst upon completion of step (b) to provide said regenerated solid composition with increased effectiveness in step (c).

2. The process of claim 1 wherein step (d) is conducted at an increased temperature relative to the temperature at which step (b) is conducted.

3. The process of claim 1 wherein said pores of said catalyst are substantially uniform in size.

4. The process of claim 1 wherein said catalyst is a small pore catalyst.

5. The process of claim 3 wherein said pores have average effective diameters of less than 5 angstroms.

6. The process of claim 1 wherein said catalyst is selected from the group consisting of layered clays, zeolitic molecular sieves, non-zeolitic molecular sieves and mixtures thereof.

7. The process of claim 1 wherein said catalyst is selected from the group consisting of non-zeolitic molecular sieves and mixtures thereof.

8. The process of claim 1 wherein said catalyst is selected from the group consisting of silicoaluminophosphates and mixtures thereof.

9. The process of claim 1 wherein said catalyst is in the range of about 1 to about 99% by weight of said solid composition and said matrix material is in the range of about 1 to about 99% by weight of said solid composition.

10. The process of claim 1 wherein said matrix material includes at least one of (1) a filler material, and (2) a binder material.

11. In a process for converting a non-olefinic feedstock containing 1 to about 6 carbon atoms per molecule which includes (a) contacting said feedstock with a solid composition comprising a small pore crystalline microporous three dimensional, catalyst having the ability to promote said conversion, and matrix material at conditions effective to convert said feedstock, to produce a hydrocarbon product containing light olefins and to at least partially deactivate said solid composition; (b) contacting said deactivated solid composition with regeneration medium at conditions effective to at least partially regenerate said solid composition; and (c) repeating step (a); the improvement which comprises (d) conditioning said solid composition in the presence of at least one added conditioning agent, said conditioning agent being substantially incapable of entering the pores of said catalyst, prior to step (a) to provide said solid composition with increased effectiveness in step (a).

12. The process of claim 11 wherein step (d) is conducted at increased temperature relative to the temperature at which step (b) is conducted.

13. The process of claim 11 wherein step (d) comprises contacting said solid composition with a feed material at conditions to chemically convert said feed material.

14. The process of claim 13 wherein said feed material is organic.

15. The process of claim 14 wherein said conditions at which step (d) is conducted are effective to crack said feed material.

16. The process of claim 14 wherein said feed material is paraffinic.

17. The process of claim 14 wherein said feed material contains about 3 to about 20 carbon atoms per molecule.

18. The process of claim 11 wherein said pores of said catalyst are substantially uniform in size.

19. The process of claim 11 wherein said pores have average effective diameters of less than 5 angstroms.

20. The process of claim 11 wherein said catalyst is selected from the group consisting of layered clays, zeolitic molecular sieves, non-zeolitic molecular sieves and mixtures thereof.

21. The process of claim 11 wherein said catalyst is selected from the group consisting of non-zeolitic molecular sieves and mixtures thereof.

22. The process of claim 11 wherein said catalyst is selected from the group consisting of silicoaluminophosphates and mixtures thereof.

23. The process of claim 11 wherein said catalyst is in the range of about 1 to about 99% by weight of said solid composition and said matrix material is in the range of about 1 to about 99% by weight of said solid composition.

24. The process of claim 11 wherein said matrix material includes at least one of (1) a filler material, and (2) a binder material.

25. In a process for converting a feedstock containing methanol, ethanol, dimethyl ether, diethyl ether, and mixtures thereof, which includes contacting said feedstock with solid particles comprising a small pore crystalline microporous three dimensional solid catalyst having the ability to promote said conversion and matrix material, said solid particles being present in the fluidized state or in a fixed bed, at conditions effective to convert said feedstock and to produce a product containing ethylene, propylene, butenes and mixtures thereof, the improvement which comprises conducting said contacting in the presence of at least one added conditioning agent comprising a basic material in an amount effective to improve the performance of said solid particles in said contacting, said conditioning agent being substantially incapable of entering the pores of said catalyst.

26. The process of claim 25 wherein said solid particles are present in the fluidized state.

27. The process of claim 25 wherein said conditioning agent is effective to improve the selectivity of said solid particles to produce said product.

28. The process of claim 25 wherein said basic material is selected from the group consisting of pyridine, pyridine derivatives, quinoline, quinoline derivatives and mixtures thereof.

29. The process of claim 25 wherein aid catalyst is in the range of about 1 to about 99% by weight of said solid particles and said matrix material is in the range of about 1 to about 99% by weight of said solid particles.

30. The process of claim 25 wherein said pores of said catalyst are substantially uniform in size.

31. The process of claim 30 wherein said pores have average effective diameters of less than 5 angstroms.

32. The process of claim 25 wherein said catalyst is selected from the group consisting of layered clays, zeolitic molecular sieves, non-zeolitic molecular sieves and mixtures thereof.

33. The process of claim 25 wherein said catalyst is selected from the group consisting of non-zeolitic molecular sieves and mixtures thereof.

34. The process of claim 25 wherein said catalyst is selected from the group consisting of silicoaluminophosphates and mixtures thereof.

35. The process of claim 25 wherein said matrix material includes at least one of (1) a filler material, and (2) a binder material.

36. The process of claim 1 wherein said feedstock comprises at least one compound selected from the group consisting of alcohols, halides, mercaptans, sulfides, amines, ethers, and carbonyl compounds.

37. The process of claim 11 wherein said feedstock comprises at least one compound selected from the group consisting of alcohols, halides, mercaptans, sulfides, amines, ethers, and carbonyl compounds.

38. The process of claim 1 wherein said basic material is selected from the group consisting of pyridine, pyridine derivatives, quinoline, quinoline derivatives and mixtures thereof.

39. The process of claim 38 wherein said feedstock is selected from the group consisting of methanol, ethanol, dimethyl ether and mixtures thereof.

40. The process of claim 39 wherein said product is selected from the group consisting of ethylene, propylene, butylenes and mixtures thereof.

41. The process of claim 37 wherein said feedstock is selected from the group consisting of methanol, ethanol, dimethyl ether and mixtures thereof.

42. The process of claim 41 wherein said product is selected from the group consisting of ethylene, propylene, butylenes and mixtures thereof.

* * * * *